US012569154B2

(12) United States Patent
Safi et al.

(10) Patent No.: US 12,569,154 B2
(45) Date of Patent: Mar. 10, 2026

(54) PATHLENGTH RESOLVED CW-LIGHT SOURCE BASED DIFFUSE CORRELATION SPECTROSCOPY

(71) Applicant: UNIVERSITY OF SOUTH FLORIDA, Tampa, FL (US)

(72) Inventors: Abdul Mohaimen Safi, Tampa, FL (US); Ashwin Bharadwaj Parthasarathy, Tampa, FL (US); Sadhu Moka, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 18/029,649

(22) PCT Filed: Sep. 28, 2021

(86) PCT No.: PCT/US2021/052419
§ 371 (c)(1),
(2) Date: Mar. 30, 2023

(87) PCT Pub. No.: WO2022/072353
PCT Pub. Date: Apr. 7, 2022

(65) Prior Publication Data
US 2023/0363657 A1 Nov. 16, 2023

Related U.S. Application Data

(60) Provisional application No. 63/155,505, filed on Mar. 2, 2021, provisional application No. 63/198,181, filed on Oct. 1, 2020.

(51) Int. Cl.
*A61B 5/026* (2006.01)
*A61B 5/00* (2006.01)

(52) U.S. Cl.
CPC .......... *A61B 5/0261* (2013.01); *A61B 5/0075* (2013.01)

(58) Field of Classification Search
CPC ... A61B 5/0261; A61B 5/0075; A61B 5/7246; A61B 2562/0242; A61B 5/0066; A61B 5/4064; G01N 2021/4797
See application file for complete search history.

(56) References Cited

U.S. PATENT DOCUMENTS 6,076,010 A * 6/2000 Boas .................. G01N 21/4795
356/337
7,061,622 B2 6/2006 Rollins et al.
(Continued)

FOREIGN PATENT DOCUMENTS

EP        0628804 A1    12/1994
WO      2019204231 A1   10/2019
WO      2022072353 A1    4/2022

OTHER PUBLICATIONS

Yodh, A. G., Kaplan, P. D., & Pine, D. J. (1990). Pulsed diffusing-wave spectroscopy: High resolution through nonlinear optical gating. In XVII International Conference on Quantum Electronics. Digest of Publ by IEEE. (Year: 1990).*
(Continued)

*Primary Examiner* — Pascal M Bui Pho
*Assistant Examiner* — Nicholas A Robinson
(74) *Attorney, Agent, or Firm* — Quarles & Brady LLP; Yakov S. Sidorin

(57) ABSTRACT
A system configured to perform the DCS-type measurements with the use of low-coherence continuous-wave (CW) light source at levels of light intensities that are substantially lower and with pathlengths through the tissue that are substantially longer than those afforded by the use of conventional methods. The method includes utilizing the optical detection system to producing signals representing interfer-
(Continued)

ence between the portion of CW light arriving through reference arm of interferometer and the sample CW light potion that has traversed the sample arm including different paths through the target tissue while switching between first and second of said different paths only by adjusting a delay in the delay line. The spatial resolution of different pathlengths of sample light through tissue is defined by coherence length of CW light.

20 Claims, 6 Drawing Sheets

(56) References Cited

U.S. PATENT DOCUMENTS

| 10,962,414 | B2 | 3/2021 | Durduran | |
| 2006/0063995 | A1* | 3/2006 | Yodh | A61B 5/0261 |
| | | | | 600/323 |
| 2011/0282331 | A1* | 11/2011 | Brennan | G01B 9/02091 |
| | | | | 606/4 |
| 2019/0053721 | A1 | 2/2019 | Boas et al. | |
| 2019/0120608 | A1* | 4/2019 | Kennedy | G01B 9/02027 |
| 2019/0336001 | A1* | 11/2019 | Zhou | A61B 5/7257 |
| 2019/0336007 | A1 | 11/2019 | Ruan et al. | |
| 2019/0336060 | A1 | 11/2019 | Shen et al. | |
| 2020/0060542 | A1 | 2/2020 | Alford et al. | |
| 2020/0225021 | A1* | 7/2020 | Wei | G01B 9/02027 |
| 2022/0361764 | A1* | 11/2022 | Sutin | A61B 5/0075 |

OTHER PUBLICATIONS

Pagliazzi M, Sekar SKV, Colombo L, Martinenghi E, Minnema J, Erdmann R, Contini D, Mora AD, Torricelli A, Pifferi A, Durduran T. Time domain diffuse correlation spectroscopy with a high coherence pulsed source: in vivo and phantom results. Biomed Opt Express. Oct. 27, 2017;8(11):5311-5325 (Year: 2017).*

International Search Report of Related PCT/US2021/052419, mailed Jan. 27, 2022, 3 pages.

Written Opinion of Related PCT/US2021/052419, mailed Jan. 27, 2022, 9 pages.

Safi, Abdul Mohaimen, et al. "Quantitative measurement of static and dynamic tissue optical properties with continuous wave pathlength resolved diffuse correlation spectroscopy." Optics and the Brain. Optica Publishing Group, 2021.

Graduate Research Symposium, "Tittle: Continuous Wave Pathresolved Diffuse Correlation Spectroscopy System for Quantifying Deep Tissue Physiology" Apr. 9, 2021.

Pagliazzi, M., et al. "In vivo time domain speckle contrast optical spectroscopy." European Conference on Biomedical Optics. Optica Publishing Group, 2019.

Borycki, Dawid, et al. "Interferometric Near-Infrared Spectroscopy (iNIRS) for determination of optical and dynamical properties of turbid media." Optics express 24.1 (2016): 329-354.

Borycki, Dawid, et al. "Reflectance-mode interferometric near-infrared spectroscopy quantifies brain absorption, scattering, and blood flow index in vivo." Optics letters 42.3 (2017): 591-594.

Pagliazzi, M., et al. "Time domain diffuse correlation spectroscopy with a high coherence pulsed source: in vivo and phantom results." Biomedical optics express 8.11 (2017): 5311-5325.

Samaei, Saeed, et al. "Time-domain diffuse correlation spectroscopy (TD-DCS) for noninvasive, depth-dependent blood flow quantification in human tissue in vivo." Scientific reports 11.1 (2021): 1817.

Sutin, Jason, et al. "Time-domain diffuse correlation spectroscopy." Optica 3.9 (2016): 1006-1013.

Kholiqov, Oybek, et al. "Time-of-flight resolved light field fluctuations reveal deep human tissue physiology." Nature communications 11.1 (2020): 391.

Devor, A. et al. Frontiers in optical imaging of cerebral blood flow and metabolism. Journal of Cerebral Blood Flow & Metabolism 32, 1259-1276, doi:10.1038/jcbfm.2011.195 (2012).

Devor, Anna, et al. "Frontiers in optical imaging of cerebral blood flow and metabolism." Journal of Cerebral Blood Flow & Metabolism 32.7 (2012): 1259-1276.

Boas, David A., and Arjun G. Yodh. "Spatially varying dynamical properties of turbid media probed with diffusing temporal light correlation." JOSA A 14.1 (1997): 192-215.

Durduran, Turgut, and Arjun G. Yodh. "Diffuse correlation spectroscopy for non-invasive, micro-vascular cerebral blood flow measurement." Neuroimage 85 (2014): 51-63.

Yu, Guoqiang, et al. "Validation of diffuse correlation spectroscopy for muscle blood flow with concurrent arterial spin labeled perfusion MRI." Optics express 15.3 (2007): 1064-1075.

Mesquita, Rickson C., et al. "Direct measurement of tissue blood flow and metabolism with diffuse optics." Philosophical Transactions of the Royal Society A: Mathematical, Physical and Engineering Sciences 369. 1955 (2011): 4390-4406.

Buckley, Erin M., et al. "Cerebral hemodynamics in preterm infants during positional intervention measured with diffuse correlation spectroscopy and transcranial Doppler ultrasound." Optics Express 17.15 (2009): 12571-12581.

Buckley, Erin M., et al. "Validation of diffuse correlation spectroscopic measurement of cerebral blood flow using phase-encoded velocity mapping magnetic resonance imaging." Journal of biomedical optics 17.3 (2012): 037007-037007.

Durduran, Turgut, et al. "Transcranial optical monitoring of cerebrovascular hemodynamics in acute stroke patients." Optics express 17.5 (2009): 3884-3902.

Favilla, Christopher G., et al. "Optical bedside monitoring of cerebral blood flow in acute ischemic stroke patients during head-of-bed manipulation." Stroke 45.5 (2014): 1269-1274.

Jain, Varsha, et al. "Cerebral oxygen metabolism in neonates with congenital heart disease quantified by MRI and optics." Journal of Cerebral Blood Flow & Metabolism 34.3 (2014): 380-388.

Yu, Guoqiang, et al. "Time-dependent blood flow and oxygenation in human skeletal muscles measured with noninvasive near-infrared diffuse optical spectroscopies." Journal of biomedical optics 10.2 (2005): 024027-024027.

Mesquita, Rickson C., et al. "Optical monitoring and detection of spinal cord ischemia." PLoS One 8.12 (2013): e83370.

Wang, Detian, et al. "Fast blood flow monitoring in deep tissues with real-time software correlators." Biomedical optics express 7.3 (2016): 776-797.

Biswas, Arindam, et al. "Fast diffuse correlation spectroscopy with a low-cost, fiber-less embedded diode laser." Biomedical Optics Express 12.11 (2021): 6686-6700.

Tamborini, Davide, et al. "Development and characterization of a multidistance and multiwavelength diffuse correlation spectroscopy system." Neurophotonics 5.1 (2018): 011015-011015.

Carp, Stefan A., et al. "Combined multi-distance frequency domain and diffuse correlation spectroscopy system with simultaneous data acquisition and real-time analysis." Biomedical optics express 8.9 (2017): 3993-4006.

Mesquita, Rickson C., et al. "Influence of probe pressure on the diffuse correlation spectroscopy blood flow signal: extra-cerebral contributions." Biomedical optics express 4.7 (2013): 978-994.

Baker, Wesley B., et al. "Pressure modulation algorithm to separate cerebral hemodynamic signals from extracerebral artifacts." Neurophotonics 2.3 (2015): 035004-035004.

Cheung, Cecil, et al. "In vivo cerebrovascular measurement combining diffuse near-infrared absorption and correlation spectroscopies." Physics in Medicine & Biology 46.8 (2001): 2053.

Farzam, Parisa, et al. "Shedding light on the neonatal brain: probing cerebral hemodynamics by diffuse optical spectroscopic methods." Scientific reports 7.1 (2017): 15786.

Kim, Meeri N., et al. "Noninvasive measurement of cerebral blood flow and blood oxygenation using near-infrared and diffuse correlation spectroscopies in critically brain-injured adults." Neurocritical care 12 (2010): 173-180.

(56)          References Cited

OTHER PUBLICATIONS

Mesquita, Rickson C., et al. "Blood flow and oxygenation changes due to low-frequency repetitive transcranial magnetic stimulation of the cerebral cortex." Journal of Biomedical Optics 18.6 (2013): 067006-067006.

Binzoni, Tiziano, et al. "Depth sensitivity of frequency domain optical measurements in diffusive media." Biomedical optics express 8.6 (2017): 2990-3004.

Bevilacqua, Frédéric, et al. "Sampling tissue volumes using frequency-domain photon migration." Physical Review E 69.5 (2004): 051908.

Borycki, Dawid, Oybek Kholiqov, and Vivek J. Srinivasan. "Interferometric near-infrared spectroscopy directly quantifies optical field dynamics in turbid media." Optica 3.12 (2016): 1471-1476.

Buckley, Erin M., et al. "Diffuse correlation spectroscopy for measurement of cerebral blood flow: future prospects." Neurophotonics 1.1 (2014): 011009-011009.

Borycki, Dawid, Oybek Kholiqov, and Vivek J. Srinivasan. "Reflectance-mode interferometric near-infrared spectroscopy quantifies brain absorption, scattering, and blood flow index in vivo." Optics letters 42.3 (2017): 591-594.

Petoukhova, Anna L., Wiendelt Steenbergen, and Frits FM De Mul. "Path-length distribution and path-length-resolved Doppler mea-surements of multiply scattered photons by use of low-coherence interferometry." Optics letters 26.19 (2001): 1492-1494.

Baker, Wesley B., et al. "Modified Beer-Lambert law for blood flow." Biomedical optics express 5.11 (2014): 4053-4075.

Durduran, Turgut, et al. "Diffuse optics for tissue monitoring and tomography." Reports on progress in physics 73.7 (2010): 076701.

Tamborini, Davide, et al. "Portable system for time-domain diffuse correlation spectroscopy." IEEE Transactions on Biomedical Engineering 66.11 (2019): 3014-3025.

Cheng, Xiaojun, et al. "Time domain diffuse correlation spectroscopy: modeling the effects of laser coherence length and instrument response function." Optics letters 43.12 (2018): 2756-2759.

Mei, Liang, Gabriel Somesfalean, and Sune Svanberg. "Frequency-modulated light scattering interferometry employed for optical properties and dynamics studies of turbid media." Biomedical Optics Express 5.8 (2014): 2810-2822.

Boas, David, Jason Sutin, and Maria Angela Franceschini. "Systems and methods for path length selected diffuse correlation spectroscopy." U.S. Appl. No. 16/079,881.

Sutin, Jason, et al. "Systems and methods for time-resolved diffuse correlation spectroscopy.".

CNIPA Office Action dated Aug. 16, 2025, Chinese patent application 2021800676347, 16 pages.

* cited by examiner

PATHLENGTH RESOLVED CW-LIGHT SOURCE BASED DIFFUSE CORRELATION SPECTROSCOPY

CROSS-REFERENCE TO RELATED APPLICATIONS

This patent application is a US national phase of pending International Patent Application No. PCT/US2021/052419 filed on Sep. 28, 2021 and now published as WO 2022/072353, which claims priority from and benefit of the U.S. Provisional Patent Applications No. 63/198,181 filed on Oct. 1, 2020 and No. 63/155,505 filed on Mar. 2, 2021. The disclosure of each of the above-identified patent applications is incorporated herein by reference.

TECHNICAL FIELD

Embodiments of the invention relate, generally, to a Diffuse Correlation Spectroscopy (DCS) methodology (used, for example, to determine various optical properties of target biological tissue and its hemodynamic perfusion characteristics) and, specifically, the DCS systems and methods that are configured to perform the DCS-type measurements with the use of low-coherence continuous-wave (CW) light sources at levels of light intensities that are substantially lower and with pathlengths through the tissue that are substantially longer than those afforded by the use of, for example, time-domain and/or interferometry-based DCS approaches that are currently employed.

SUMMARY

Embodiments of the invention provide methodology of acquiring the sought-after DCS-type information representing the target tissue (such as, for example, photon time of flight distribution and pathlength resolved autocorrelation functions) with the use of a DCS-type approach in which the resolution (or separability) of the measurement according to pathlengths of used light through the target tissue is performed simply by adjusting a time-delay between two portions of such used light delivered to two spatially-separated surface areas of the tissue.

According to the idea of the invention, the measurements are carried out with a system that employs a necessarily continuous-wave (CW) light source configured to generate low-coherence light (such as, for example, spatially and/or temporally multi-mode laser diodes, LEDs, in contradistinction with the use of highly-coherent laser sources of the systems of related art) and that can employ an otherwise conventional DCS optical detection system. A skilled artisan having an advantage of this disclosure will readily appreciate that operating the DCS system in the necessarily CW light regime allows the user to necessarily improve the signal-to-noise ratio of the measurement and, therefore, allows the user to carry out a measurement along a light path with longer pathlength through the target tissue than that afforded by the existing methodologies utilizing long-coherence-length pulsed/modulated laser light sources, thereby enhancing measurement sensitivity of the proposed DCS instrument to tissues located at greater depths (for example, deeper in the cortex) as compared with shallower-disposed portions of the tissue that can be reliably measured with existing systems. Furthermore—and in stark contradistinction with existing DCS-type system—the use of the low-coherence length light source provides the user with flexibility of controlling the paths along which light passes through the tissue with pathlength increments defined by (and, if needed, substantially equal to) the coherence length of light generated by such source. Notably, an embodiment of the proposed system can be implemented as an 'add-on' to existing DCS instruments, thereby equipping the systems of related art with an ability (currently missing or at least severely limited) to perform blood flow measurements, for example with pathlength and/or depth sensitivity.

Accordingly, embodiments of the invention provide a method for performing a DCS measurement of a target tissue, which method includes a step of directing a first portion of light (that has a coherence length and that is generated by a necessarily continuous-wave light source) to a first surface area of the target tissue while directing a second portion of the same light to an optical detection system through a delay line. The method further includes a step of receiving light from the first portion of light (after such light has traversed the target tissue) at the second surface area of the tissue, in the form of sample light, and directing this sample light to the optical detection system. Here, the first and second surface areas of the tissue are generally spatially separated from one another by a separation distance. The method additionally includes a step of producing (at the optical detection system) signals that represent interference between the second portion of light and the sample light (which sample light has traversed different paths through the target tissue between the first and second surface areas) while switching between first and second of such different paths only by adjusting a delay in the delay line. (For the purposes of the disclosure, and unless expressly defined otherwise, the term interference is used to conventionally imply, describe, and/or relate to a situation when a combination of two or more electromagnetic waveforms (two or more optical waves, for example) produce a resultant wave in which the displacement is either reinforced or canceled. In other words, the terms interference and interfere and similar terms refer to a phenomenon in which two coherent with each other waves superpose to form a resultant wave of greater, lower, or the same amplitude.)

In at least one implementation of the method, the act of directing the first portion of light to the first surface area includes at least one of: directing the first portion of light having a coherence length of at least 0.05 mm, or at least 0.1 mm, or in specific case between about 0.1 mm and about 0.9 mm; and directing the first portion of light generated by the necessarily continuous-wave light source that is configured to form spatially multi-mode distribution of light it generates. Alternatively or in addition, the switching between first and second of the different paths only by adjusting time delay in the delay line may include switching between the first and second of the different paths with pathlength resolution necessarily defined by the coherence length of light generated by the necessarily CW light source.

Alternatively or in addition, and in substantially any implementation of the method, at least one of the step of directing the first portion of light and the step of directing the second portion of light may include transmitting light through a free space and/or through an optical fiber. Alternatively or in addition, and substantially in any implementation of the method, the act of switching light propagating through the target tissue between the first and second of the different paths through such tissue may include changing a pathlength of the light through the target tissue with an increment substantially equal to the coherence length.

Alternatively or in addition, and substantially in every implementation of the method, the necessarily continuous-wave light source may be configured to generate light having such a degree of coherence that a signal from the signals representing the interference of light at the optical detection system represents interference between the second portion of light and the sample light that has traversed a volume of the target tissue at depths not only 1-3 cm (comparable to the depths teachable by the DCS measurements carried out with methodologies if related art) but also at depths in excess of 3 cm (for example, 3-4 cm, or even deeper than 4 cm in some implementations) below the surface of the tissue. Alternatively or in addition, and practically in every embodiment of the method, the necessarily continuous-wave light source may be configured to generate light having such a degree of coherence that the sample light and the second portion of light interfere with one another at the optical detection system while at least one of the following conditions is satisfied: the sample light has been collected at the second surface portion that is separated from the first surface portion by the fixed separation distance (and at least one case—the separation distance exceeding 2.5 cm; and the sample light represents light from the first portion of light that has traversed a pathlength between the first and second surface areas that is greater than a separation distance (and, in at least one case—of at least 20 cm).

Furthermore, any embodiment of the method may additionally include a step of determining intensity autocorrelation functions and parameters (such absorption, light scattering, flow of moving particle) characterizing tissue traversed by light along each of the different paths through the target tissue with the use of electronic circuitry that is specifically configured to receive said signals from the optical detection system. (In at least one case, such electronic circuitry may be configured as a programmable processor, for example a computer processor.)

In a specific version of the latter case, said the step of determining may include a process of numerical fitting of such intensity autocorrelation functions to a negative exponential function that depends on a wave vector value representing the sample light but, at the same time, is independent from an absorption coefficient of said the target tissue; and/or additionally include a step of determining values of intensities of the sample light for each of the different paths such light traversed through the target tissue.

Alternatively or in addition, and substantially in every implementation, the method may include a step of recording a parameter of a blood flow through the target tissue as a function of a depth of a given path, from the different paths, in the target tissue (and, optionally, producing a report representing such a parameter—for example, in a visually-perceivable fashion). In such a case, the process of recording a parameter of the blood flow may include recording such a parameter at a rate of lower than 20 Hz; or between 20 Hz and 100 Hz; or greater than 100 Hz, to name just a few of possibilities.

Alternatively or in addition, and substantially in every embodiment of the method, the method is configured to be devoid of using (that is, without using) a source of pulsed light or a light source configured to generate modulated light. The scope of the invention includes a corresponding DCS measurement system configured to operate such as to implement the method as summarized above.

BRIEF DESCRIPTION OF THE DRAWINGS

For a more complete understanding of the disclosure, reference is made to the following detailed description and accompanying Drawings, of which.

Figure 1:
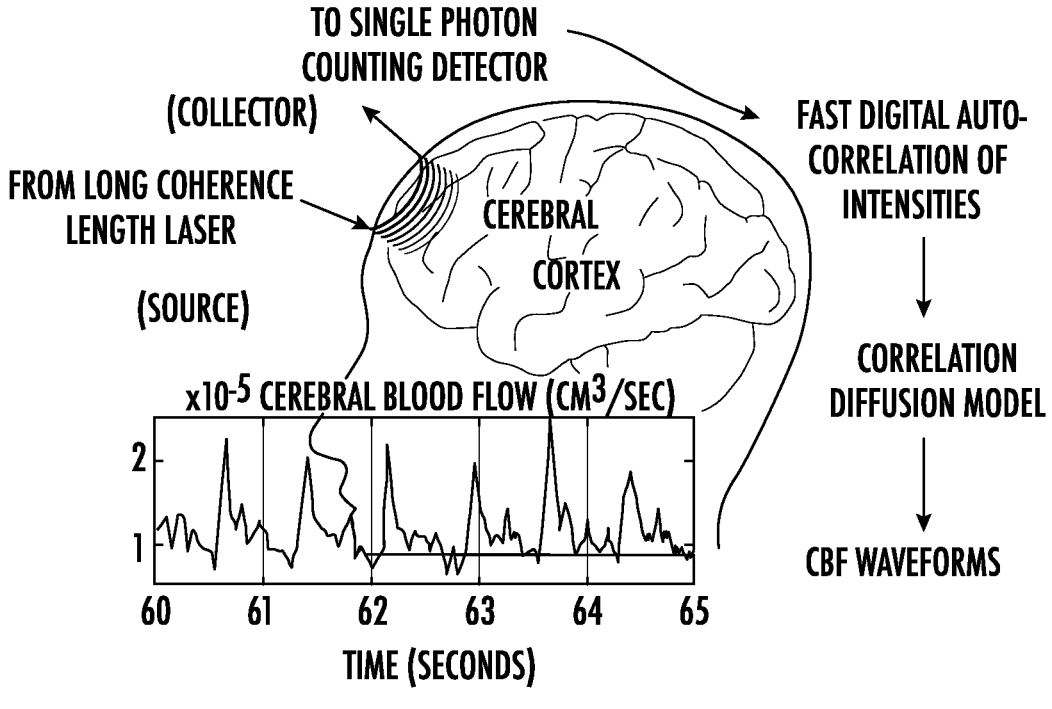
FIG. 1 illustrates schematically a noninvasive measurement of cerebral blood flow (CBF) waveforms with the use of a conventionally-configured Diffuse Correlation Spectroscopy (DCS) system.

Generally, the sizes and relative scales of elements in Drawings may be set to be different from actual ones to appropriately facilitate simplicity, clarity, and understanding of the Drawings. For the same reason, not all elements present in one Drawing may necessarily be shown in another. While specific embodiments are illustrated in the figures with the understanding that the disclosure is intended to be illustrative, these specific embodiments are not intended to limit the scope of invention implementations of which are described and illustrated herein.

DETAILED DESCRIPTION

Continued biomedical research requires knowledge of data representing the state of health of a target tissue which, in turn, demands that technologies enabling noninvasive in vivo measurements of tissue functions not only possess accuracy and precision, but are also operationally stable while affording repeatable and cost-efficient performance. A skilled artisan knows well that blood flow is one important indicator of tissue health, since characterization of the blood flow directly informs the clinician about the status of oxygen and/or nutrient supply to the target tissue. Therefore, the ability to easily monitor blood flow—and, in particular, outside of clinical environment—has practical significance in treatment of a variety of diseases including strokes, traumatic brain injuries, cancers, and peripheral vascular disorders.

A skilled artisan knows from related art that optical methods based on the diffusion of light through tissue are well suited for noninvasively determining the state of tissue health, for applications ranging from bedside clinical monitoring of physiology to basic science interrogations of tissue function. Optical techniques possess the ability to noninvasively probe a wide variety of tissue types, and they can continuously and safely (optics is non-ionizing) measure biomarkers of tissue health from structures a few centimeters below the surface, without use of any contrast agents. 'Clinical' optical measurement techniques use diffusion of light through tissue to probe tissue vasculature (generally limited to the depths of at most 1-to-3 cm below skin surface) with flexible fiber optic probes placed on the tissue surface. Amongst a broader class of Near Infrared Spectroscopy (NIRS) instruments, the technique of DCS assesses the tissue blood flow from temporal intensity fluctuations of highly coherent light that has diffused through the tissue.

The DCS methodology has rapidly become the method of choice for portable bedside monitoring of deep tissue blood flow. DCS facilitates the sensing and quantification of flow in tissue microvasculature (arterioles) as a blood flow index (BFI). In comparison with other bedside flow monitors, such as Doppler ultrasound, the DCS approach is sensitive to all moving particles in the sampling area, and therefore, measured blood flow is especially well correlated with microvascular flow. (The DCS blood flow indices have been validated against a variety of gold standard modalities including Doppler ultrasound and MRI, and its utility has been demonstrated for noninvasive deep tissue measurements in adult/pediatric brain, muscle, and spinal cord.)

FIG. 1 schematically illustrates a standard, performed according to currently-employed in related art approach DCS measurement (as shown—of the cerebral blood flow waveforms). Here, near infrared light received by the target tissue at a source location from a long coherence length diode laser (such as a 785 nm, 100 mW source produced by Toptica Photonics, for example) is used to illuminate the cerebral cortex using custom fiber optics. Light, multiply scattered upon propagation through the tissue, is collected from the tissue using single mode fiber optics (at a collector location usually 1-4 cm away from the location of the source) and is directed to a single photon counting avalanche photodiode modules (for example, produced by Excelitas SPCM4AQC, Canada) that generate a TTL (transistor-transistor logic) pulse for each of detected photons. Changes in the optical pathlength of light diffusing through the tissue (i.e., due to scattering of moving particles/red blood cells) impart temporal fluctuations in the intensity recorded by the detector of the used optical detection system, which are formally quantified by computation of a digital normalized intensity autocorrelation function $g_2(\tau)$. A quantitative and direct index of blood flow is then estimated (see, for example, Boas, D. A. & Yodh, A. G; in *J. Opt. Soc. Am. A* 14, 192-215 (1997) or Durduran, T. & Yodh, A. G., in *NeuroImage* 85 Pt 1, 51-63, doi:10.1016/j.neuroimage.2013.06.017; 2014) by fitting the measured $g_2(\tau)$. to mathematical models appropriate to the measurement geometry (see, e.g., Wang, D. et al., in *Biomedical optics express* 7, 776-797, doi:10.1364/BOE.7.000776; 2016). Recently, the digital software processing schemes were employed to increase CBF measurement speeds 100 fold to ~100 Hz, facilitating the first noninvasive optical measurements of pulsatile CBF 'waveforms' (as shown in FIG. 1). (See, for example, Biswas, A. et al., in *Clinical and Translational Biophotonics*. JW3A. 20 (Optical Society of America); or Tamborini, D. et al., in *Neurophotonics* 5, 011015, doi:10.1117/1.NPh.5.1.011015; 2017). These measurements are similar to those from TCD (transcranial Doppler ultrasound), but they represent perfusion in the cerebral microvasculature, are simpler to measure, and offer enhanced patient comfort. This newfound ability to measure pulsatile CBF dynamics permits a new class of measurements with optics.

However, conventionally-structured DCS methodology suffers from critical limitations that inhibit robust clinical use. DCS—like most optical techniques—is commonly-recognized to be affected by partial volume effects, i.e., the sensitivity of CBF measurement to cerebral tissues is reduced by flow changes in the superficial layers. More specifically, the $g_2(\tau)$. is detected from an ensemble of light pathlengths from different tissue depths—that is, this normalized intensity autocorrelation function is determined as averaged over the multiple pathlengths of light through the tissue Thus—and in reference to the specific application of use of the DCS to assess the cerebral blood flow, as per FIG. 1—the measured blood flow is more sensitive to superficial tissues such as the presence of scalp/skull (which are sampled with higher probability) rather than the brain itself (which are sampled with lower probability). In the past, the present inventors have proposed (see, for example, Baker, W. B. et al., in *Neurophotonics* 2, 035004, doi:10.1117/1.NPh.2.3.035004; 2015) simple interventions and multi-layered tissue models to account for these effects—but these remain not necessarily practical for long-term continuous clinical monitoring.

Secondly, as a skilled artisan well knows, conventionally-structured DCS requires in-situ measurements of tissue optical properties to improve the fidelity of CBF estimates and facilitate robust comparisons between measurement sites/patients. As a result, conventional DCS instruments are often accompanied and/or complemented with a second, independent and distinct optical instrument to measure tissue optical properties into a hybrid probe. The result of this hybrid arrangement is 2× increase in cost of the overall measurement system (as compared with the conventional DCS apparatus alone), and reduced instrument portability (~3× larger probes, limiting regular use in spatially constrained applications like neonates, spine, and critical care). Yet a more significant concern remains the fidelity of the so-performed hybrid optical measurements. Even with collocated sources and detectors, inherent differences in measurement geometry leads to Diffuse Optical Spectroscopy (DOS) and DCS instruments sampling different—not the same!—tissue volumes (see, for example, Binzoni, T. et al. Depth sensitivity of frequency domain optical measurements in diffusive media. *Biomed. Opt. Express* 8, 2990-3004, doi:10.1364/BOE.8.002990; 2017); or Bevilacqua, F., et al.; Sampling tissue volumes using frequency-domain photon migration. *Phys. Rev. E* 69, 051908, doi:10.1103/Phys. Rev. E. 69.051908; 2004), thereby inevitably resulting in errors in estimation of blood flow, tissue oxygen saturation, or both. Differences in sampling volume are especially significant in realistic human tissues (e.g., skin) that are heterogeneous. For example, in cerebral measurements, scalp, skull, and brain tissues have significantly different optical properties. As such, DCS and multi-distance DOS) may sample different volume fractions of these tissues. These effects further confound errors of multi-distance measurements of tissue hemodynamics.

Even the recently introduced Time-Domain DCS and interferometric NIRS measurement methodologies while measuring tissue optical properties based on photon diffusion time of flight (DTOF) to improve the fidelity of blood flow measured with DCS, necessarily require the use of specialized pulsed/modulated laser sources with high temporal coherence and speed improvements to traditional DCS detectors in order to attempt to produce pathlength resolved measurements of DCS intensity autocorrelation functions.

In stark and advantageous contradistinction with related art, the present disclosure describes various embodiments of systems and methods for measuring of blood flow with a specifically—in a particular manner—pathlength-resolving Diffuse Correlation Spectroscopy (PR-DCS) instrument configured for depth-sensitive assessment of parameters representing blood flow (such as, for example, pulsatile cerebral blood flow, or CBF). The specific nature of the pathlength resolution provided by the discussed below PR-DCS apparatus manifests in the fact that the spatial increment with which different paths traversed by light through the target tissue subject to the measurement is substantially equal to the coherence length of the necessarily continuous-wave light of the low-coherence light source chosen to be used in such apparatus.

Embodiments of the invention relate, generally, to a diffuse correlation spectroscopy methodology (used, for example, to determine various optical properties of target biological tissue and its hemodynamic perfusion characteristics) and, specifically, the DCS systems and methods that are configured to perform the DCS-type measurements with the use of low-coherence CW light sources at levels of light intensities that are substantially lower and selectively with pathlengths through the tissue that are substantially longer than those afforded by the use of, for example, time-domain and/or interferometry-based DCS approaches that are currently employed.

To this end, persisting problems of inherent instability of operation, associated high levels of measurement noise, and need to use relatively high levels of intensity of light caused by a need to necessarily utilize long coherence length pulsed or at least amplitude-modulated light sources to perform the DCS-type measurements according to methodologies currently used in related art are overcome by configuring a measurement system with a necessarily CW light source (that is, which is necessarily devoid of operation in the pulsed and/or amplitude modulate regime) that has a short-coherence length and/or that is partially coherent. The low level measurement noise floor afforded by such configuration allows the measurement to be performed over longer path lengths through the tissue and/or detection of the target species at lower levels of concentration in the target tissue and/or detection of the target species at greater depths in tissue (in advantageous contradistinction with the existing methodologies).

Furthermore, the use of the low-coherence source in a Mach-Zehnder-type interferometric configuration of an embodiment of the invention enables a practically advantageous—over the methods of related art—flexibility of coherence gating of the light source. (Such coherence gating manifests in causing the measurement to be necessarily pathlength resolved by simply and only adjusting the optical delay between the signal and reference portions of light directed at the target tissue from the low coherence source of light.) Moreover, the use of the proposed methodology manifests in avoiding altogether—in contradistinction with the methodologies of related art—the complementary (and, conventionally near-infrared spectroscopy, or NIRS measurement) to be performed with a separate, independent instrument to obtain the in-situ high-fidelity measurement data.

Figure 2:
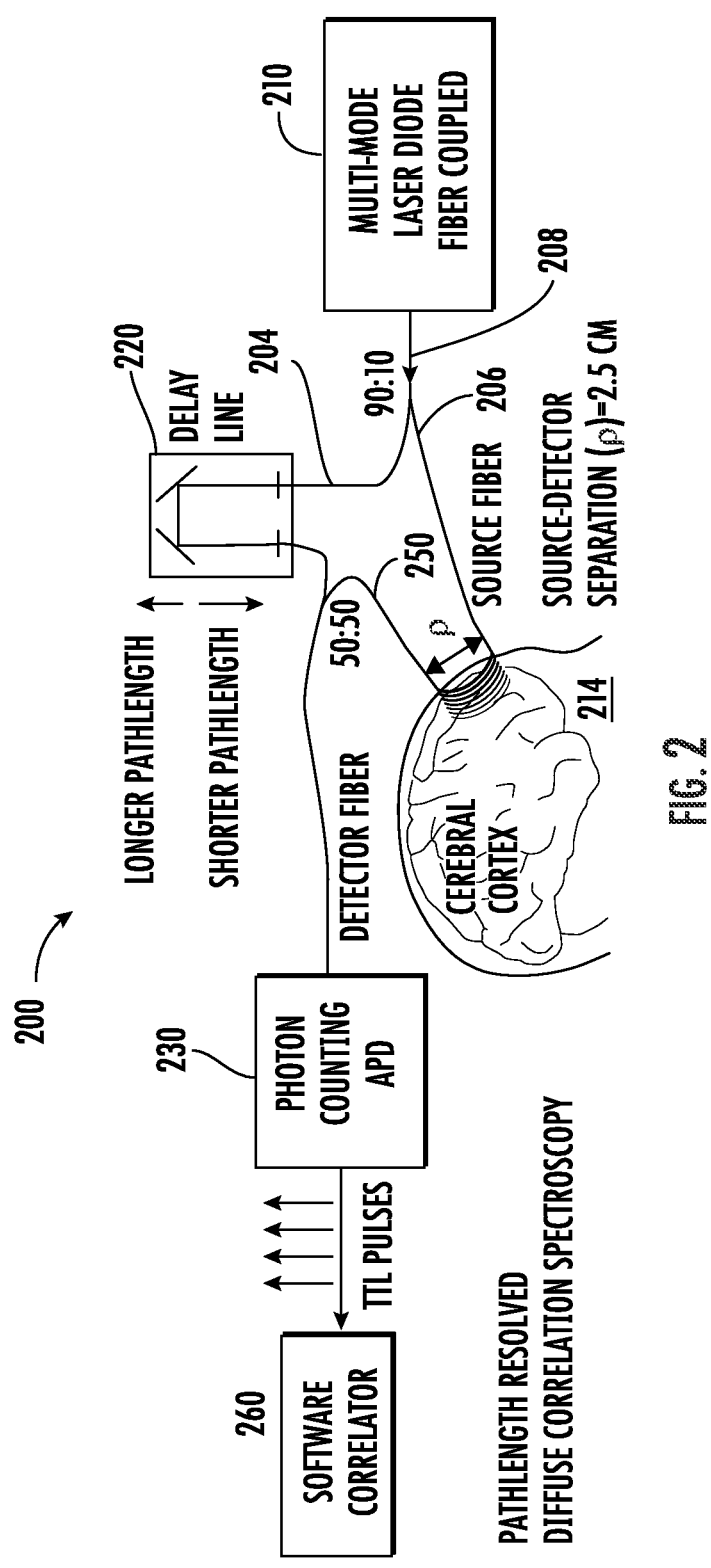
FIG. 2 shows a schematic of an embodiment of the invention configured to effectuate pathlength resolved Diffuse Correlation Spectroscopy (PR-DCS) measurements in absence of pulsed or modulated source of light and without the need to use highly coherent light source.

In various embodiments of the implementation of the idea of the current invention, the pathlength resolved measurement of the target species of the tissue (for example, the CBF flow) turns on coherence gating—implemented with the use of a delay line configured (at least in the example of FIG. 2) as a Mach-Zehnder interferometer. FIG. 2 provides a schematic 200 of PR-DCS methodology configured according to the idea of the invention, in which corresponding portions 204 and 206 of the light output 208 from a necessarily CW (and, optionally, a spatially multi-mode and/or spectrally broadband) light source 210 are directed to a programmable delay line 220 (and though it—towards the optical detection system 230) and to the sample (target tissue) 214 (and through it—towards the optical detection system 230), respectively. In the example of FIG. 2, the delay line 220 is disposed in a reference arm of the set-up configured as a Mach-Zehnder interferometer. A standard DCS detector (optical detection) arrangement or system 230 can be used to record the heterodyne interference between the optical signal arriving to the optical detection system 230 along the sample arm of the employed interferometric arrangement (which incorporates the sample 214) and that arriving along the reference arm (which incorporates the delay line 220). Depending on the specifics of a particular implementation, light portions propagating through the sample and reference arms of the apparatus can be delivered through free space, optical fibers, or both—to name just a few of possibilities.

A typical off-the-shelf continuous wave partially coherent laser diode (such as, for example, L808P0500MM, Thorlabs, NJ) featuring a nominal coherence length of from about 0.1 mm to about 0.2 mm or so (or at least 0.1 mm; in one example 0.5 mm, as measured with high-resolution spectrometer) can be employed as a light source 210. As shown in this specific example 200, one portion of the light output the laser diode 210 is coupled to a 90:10 multi-mode fiber coupler; the distal end of the 90% arm (sample arm) optical fiber channeling light 206 is directed to the tissue surface, while the 10% arm (reference arm) optical fiber channeling light 204 is directed to a combination of reflectors forming the variable delay line 220 mounted on a translation stage. It is understood that, generally, the delay line 220 is a device producing a specific desired delay in the transmission of a signal through such line. Light collected from the tissue (as shown—at a location separated by a distance $\rho$ about or greater than 2.5 cm away from the location at which light portion 206 was delivered to the tissue) is collected with another single-mode fiber element 250, recombined (99:1 ratio) with a portion of light delivered from the delay line 220, and directed to the optical detection system 230. A custom software correlator device 260 (which may optionally be implemented in LabVIEW with the use of appropriate programmable electronic circuitry) is configured to compute the intensity autocorrelation functions in real-time at various measurement rates—for example, at 20~100 Hz.

The employed DCS detector system 230 is configured to measure the mixture of electric fields arriving from the sample arm ($E_S(t)$) and the reference arm ($E_R(t)$)) arms, i.e., to produce a signal representing the optical intensity $I(t)=|E_S|^2+|E_R|^2+E_SE_R^*+E_RE_S^*$, where $E_S$ represents the superposition of sample light fields that have travelled multiple pathlengths through the tissue and $E_R$ represents the reference light field arriving to the system 230 from the delay line 220. Understandably, coherent interference of the sample and reference fields occurs only between fields that have traveled the same pathlength—thus, pathlength specific detection is necessarily achieved in the embodiment of the invention by simply varying (and in one case—varying only) the length of the reference arm—in one case, by varying the amount of delay introduced by the delay line 220. The intensity detected at 230 can be approximated as $I(s, t)=I_0+I_{DCS}(s, t)$, where $I_0$ is an incoherent addition of light fields arriving from the sample and reference arms that are not pathlength matched. $I_0$ is a constant (approximately) that can be directly measured as the sum of the average intensities with the sample and reference arms blocked (i.e. under conditions $E_S=0$, $E_R=0$). When $E_S=0$, $I(t)=|E_R|^2$ and when $E_R=0$ $I(t)=|E_S|^2$ both of which conditions represent incoherent addition of the respective light fields; therefore, $I_0\approx|E_S|^2+|E_R|^2$. $I_{DCS}(s, t)$ is the (heterodyne) pathlength-matched interference term with temporal intensity fluctuations brought about by moving particles in the sample, around/about the selected pathlength and within the coherence length of the laser. Autocorrelation of $I(t)$ yields the pathlength-resolved intensity autocorrelation function $g_2(\tau, s)=1+\beta(s)|g_1(\tau, s)|^2$, where $\beta(s)$ is the pathlength-dependent instrumentation/speckle averaging factor, $\tau$ is the correlation delay time, S is the light pathlength through the target tissue, and $g_1(\tau, s)$ is the pathlength-resolved electric field autocorrelation function. Notably, the resolution between different pathlengths of light in the sample arm through the target tissue that can be detected and implemented in an embodiment is defined by (and is substantially equal to) the coherence length of light produced by the CW source 210. Fitting $g_1(\tau, s)$ to a negative exponential model, $g_1(\tau, s)=\exp(-2\mu_s'Fk_0^2s\tau)$, yields estimates of blood flow (F). Here, $\mu_s'$ is the tissue reduced scattering coefficient and $k_0$ is the wave vector of used light. Note that $g_1(\tau, s)$ is dependent only on F and $\mu_s'$ and is independent from the tissue absorption coefficient $\mu_a$. Since $\mu_s'$ is typically constant in the tissue, pathlength-resolved measurements of relative blood flow changes are substantially insensitive to baseline tissue optical properties. Furthermore, the average of the measured intensity $I_{DCS}(s, t)=\langle I_{DCS}(s, t)\rangle$ can be further converted to time-resolved diffuse reflectance data by recognizing that photon time-of-flight in target tissue is $\delta t=s/v$, where v denotes the speed of light in the tissue. Thus, $I_{DCS}(S) \rightarrow I_{DCS}(t)$, which—when appropriately normalized—yields diffusion time-of-flight curves that can be fit to a time-domain solution of the photon diffusion equation (see, for example, Durduran, T., et al.; Diffuse optics for tissue monitoring and tomography, *Reports on progress in physics* 73, 076701, doi:10.1088/0034-4885/73/7/076701; 2010) to estimate tissue optical properties, $\mu_a$ and $\mu_s'$.

Figure 3:
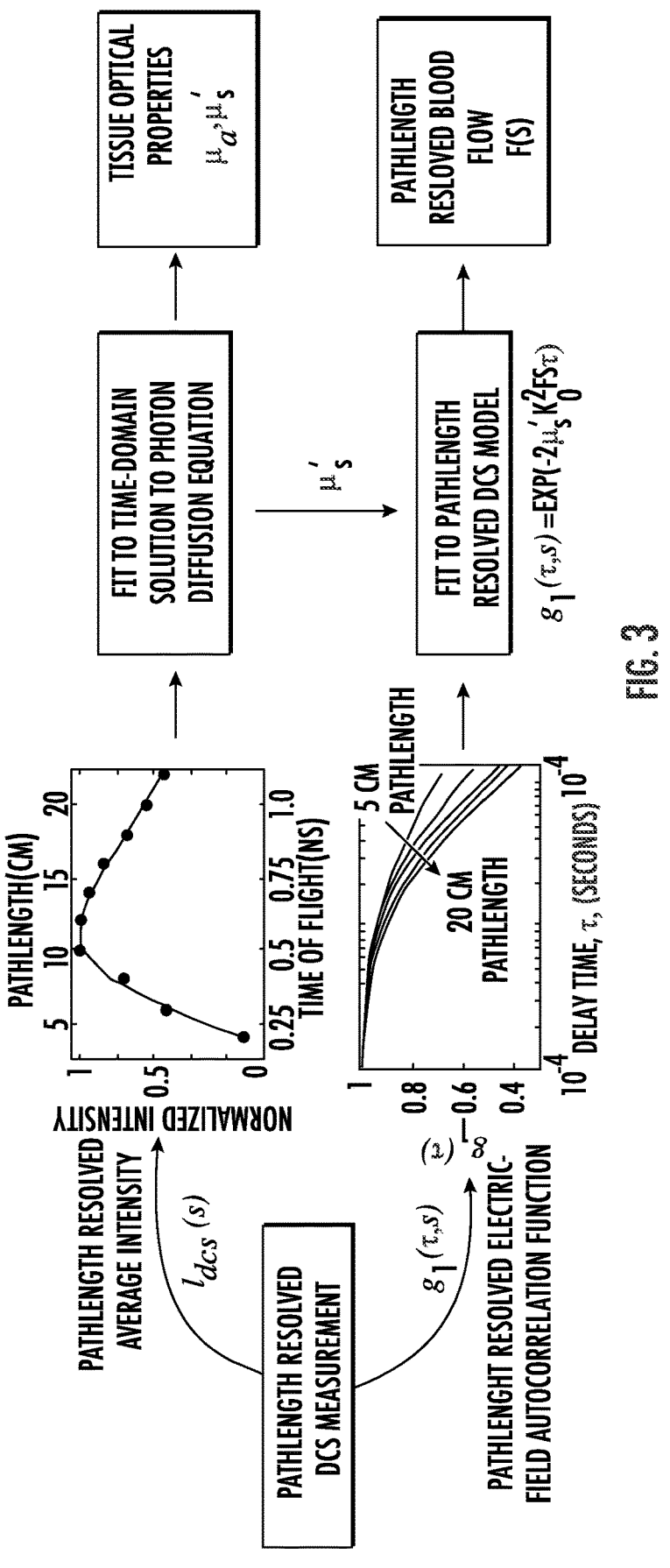
FIG. 3 depicts an example of the data analysis scheme for the disclosed PR-DCS methodology according to an embodiment of the invention.

FIG. 3 schematically illustrates an example of the data analysis flow for the embodiment of the proposed PR-DCS methodology, as discussed above Accordingly, with the use of an embodiment of the invention, a single measurement—not a combination of two measurements required by related art—yields both the pathlength-resolved average intensities (top row of FIG. 3, used to estimate optical properties of the tissue) and electric field autocorrelation functions (bottom row of FIG. 3, used to estimate moving particles in the tissue—for example blood flow). Once optical properties are computed, fast CBF measurements can be performed at a specific set/desired pathlength of light (in the sample arm of the embodiment of FIG. 2) through the tissue 214. Notably, relative CBF measurements are independent from optical properties, since $\mu_s'$ is a constant. As such, FIG. 3 presents an example of data processing protocol for fast, in vivo, depth-sensitive measurements of blood flow, in which the DCS intensity autocorrelation functions and average intensities for multiple pathlengths are simultaneously. For a spatial separation, along the surface of the target tissue 214, between the area at which the light in the sample arm is used to irradiate the tissue and the area from which the sample light is collected from the tissue, of, for example, 2.5 cm, these measurements span the range of pathlengths from about 5 cm to about 30 cm. Light propagating through the tissue along paths with pathlengths in excess of 20 cm selectively, with the pathlength resolution defined by the coherence length of employed light, samples the volumes of the tissue located as deep as 3 cm to 4 cm below the tissue surface, which is not achievable by related art employing the highly coherent light source. (As was already alluded to above, pathlength resolved average intensities can be further fit to a time-domain photon diffusion solution to first estimate tissue optical properties ($\mu_a$ and $\mu_s'$), while the pathlength-resolved intensity autocorrelation functions are used to estimate flow as a function of pathlength/tissue depth). Then, the reference arm can be fixed with a desired pathlength (depending on the tissue depth of interest), to record high-speed (for example, at 20~100 Hz) depth-sensitive changes in blood flow.

Figure 4A:
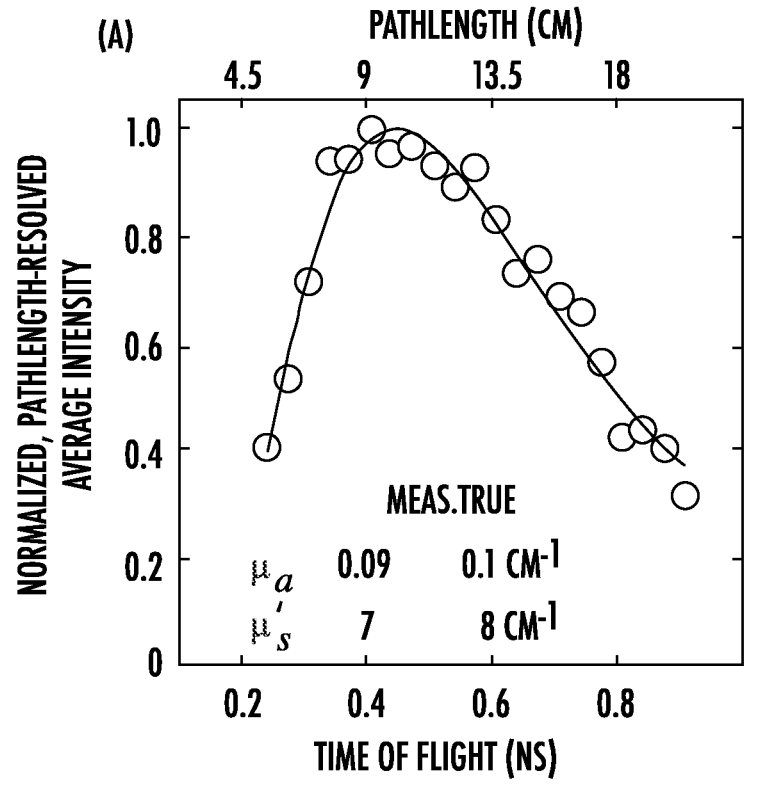
FIGS. 4A, 4B, 4C, 4D, and 4E present the results of experimental validations of pathlength resolved Diffuse Correlation Spectroscopy (PR-DCS) methodology carried out according to the idea of the invention.
Figure 4B:
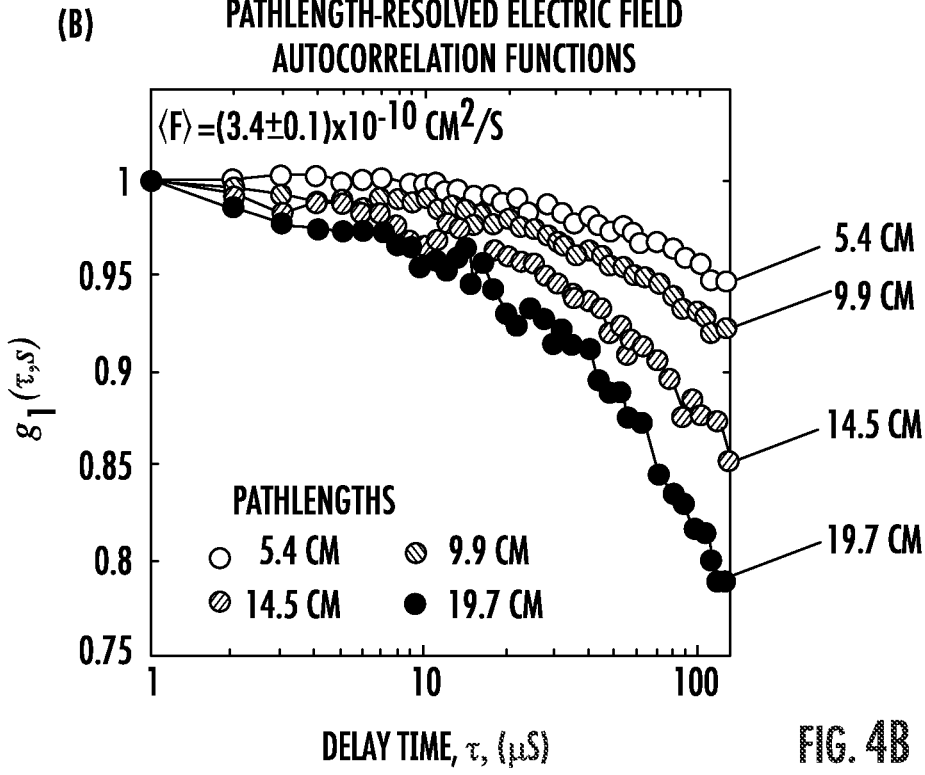

FIGS. 4A, 4B, 4C, 4D, and 4E present some experimental validation of the use of an embodiment of Pathlength Resolved Diffuse Correlation Spectroscopy methodology discussed above, demonstrating both the feasibility and workability of pathlength-resolved blood flow measurements by estimating the static (as shown in FIG. 4A) and dynamic (as shown in FIG. 4B) optical properties of a semi-infinite tissue-simulating phantom (made of intralipid and India ink, with known values of $\mu_a=0.1$ cm$^{-1}$ and $\mu_s'=8$ cm$^{-1}$). Per the idea of the invention, the PR-DCS measurements were performed with a source-detector separation of $\rho=2.5$ cm and integration time of 1 second.

Specifically, FIG. 4A displays the diffusion time-of-flight (DTOF) curve obtained by an analysis of pathlength-resolved average intensities (indicated with circles) fit to a photon diffusion model (a time-domain solution to the diffusion equation; black line), such that optical properties ($\mu_a=0.09$ cm$^{-1}$, $\mu_s'=7$ cm$^{-1}$) of this homogeneous tissue-simulated phantom, which were recovered to within 10% of their true values.

FIG. 4B shows representative pathlength-resolved electric field autocorrelation functions, assessed with an embodiment of the invention as discussed above and fit to a DCS negative exponential model to estimate blood flow. Blood flow index, $\langle F\rangle=(3.4\pm0.1)\times10^{-10}$ cm$^2$/s (in units of diffusion), was found to be substantially constant (within about 3%) across a multiplicity of different pathlengths, as a skilled artisan should expect in this homogenous semi-infinite tissue phantom.

Figure 4C:
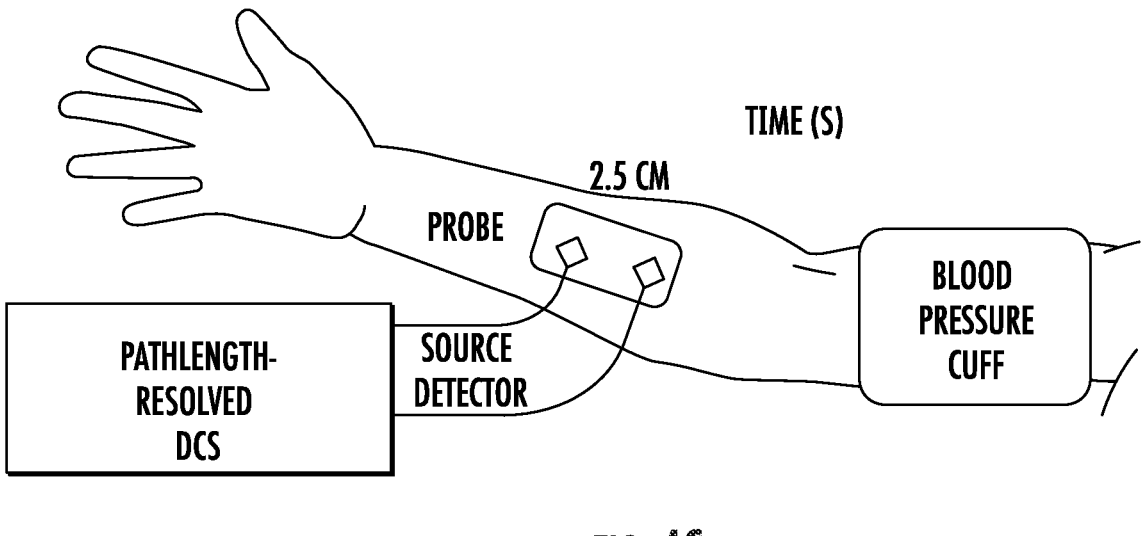

The schematic presented in FIG. 4C demonstrates the ability of the proposed methodology to measure depth-sensitive blood flow with an in vivo arm cuff ischemia experiment. Here, the PR-DCS measurements were performed on an arm of a healthy volunteer with a source-detector separation $\rho$ of at least 2.5 cm and at light pathlengths of 5.4 cm (short) and 20.5 cm (long) and longer.

Figure 4D:
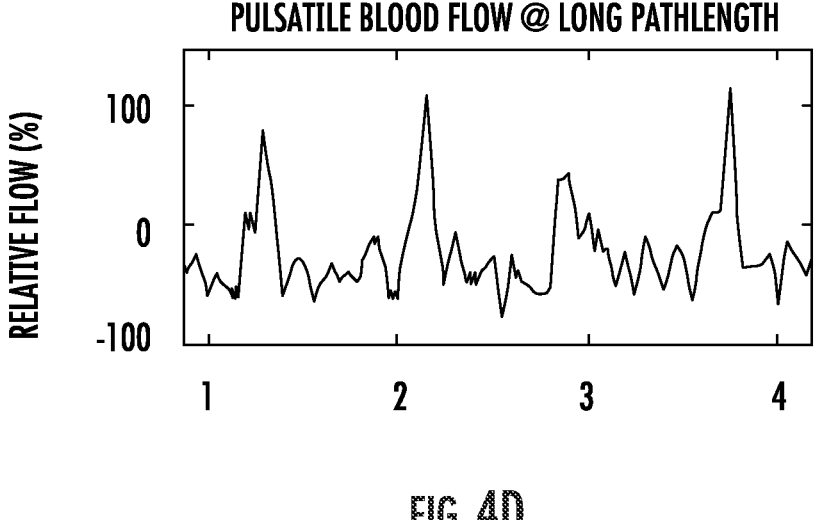

FIG. 4D presents a representative time course of pulsatile blood flow measured in the arm of a volunteer with the embodiment of PR-DCS at a 20.5 cm pathlength and a 20 Hz blood flow measurement rate. Based on assessment of FIG. 4D, a skilled person will appreciate that the blood flow pulsatility is clearly resolved, thereby demonstrating a high signal-to-noise ratio of the proposed approach. To the inventors' knowledge, this demonstration was the first pulsatile pathlength-resolved blood flow measurement with DCS.

Figure 4E:
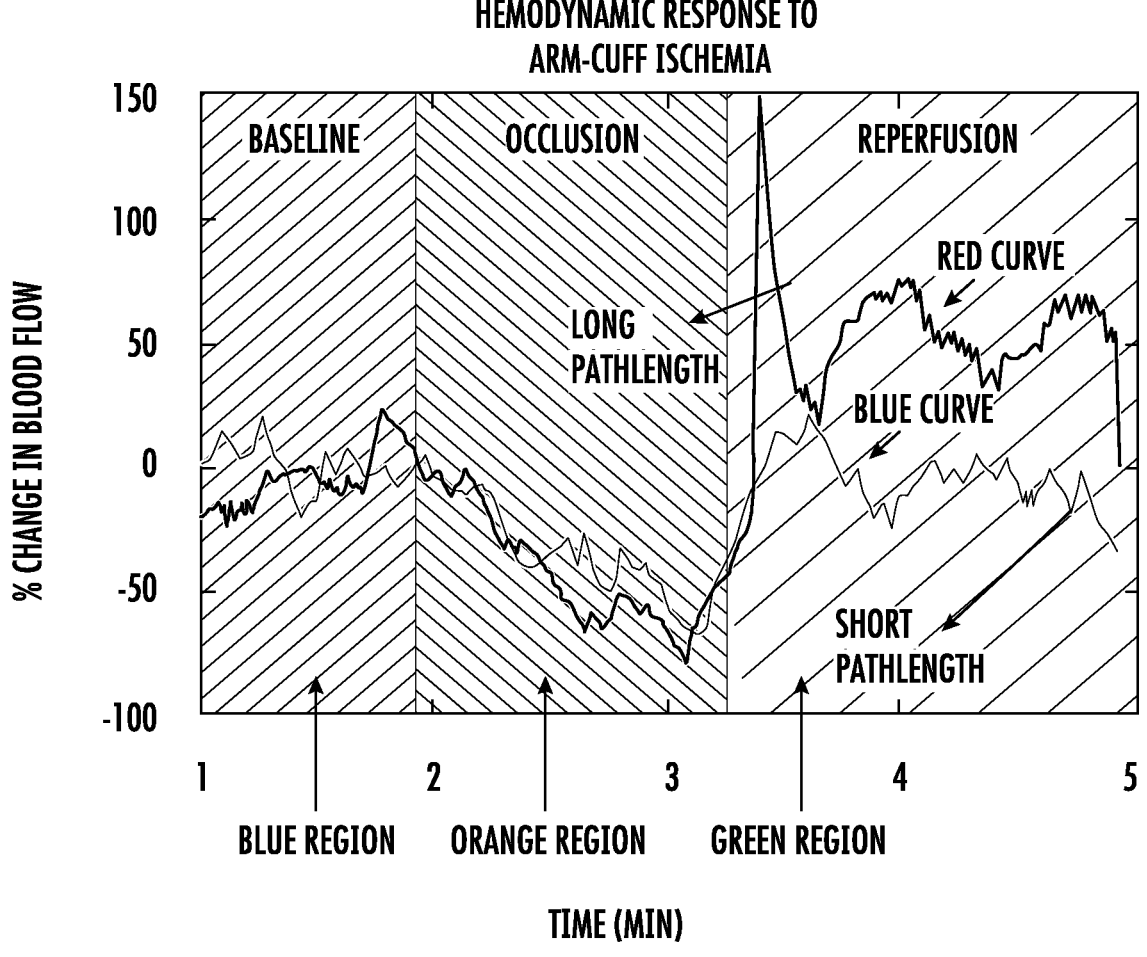

Additionally, FIG. 4E illustrates relative changes in arm blood flow during arm-cuff ischemia measured at 1 Hz with both long and short pathlengths for 1-minute baseline (represented by "blue region" of the plot), an approximately 2-minute occlusion (represented by the "orange region" of the plot), and 2-minute recovery (represented by the "green region" of the plot). Here, red and blue curves respectively indicate flow changes at 20.5 and 5.4 cm pathlengths respectively. Hemodynamic response and reperfusion peak observed at the long pathlength (red curve) is typical of a response from larger blood vessels in the muscle that lie deeper within the tissue. On the other hand, the corresponding response observed at the shorter pathlength from smaller, shallower blood vessels is stunted, which indicates that the tissue sampled is primarily microvasculature in the skin. These preliminary experiments clearly demonstrate that the embodiment of the PR-DCS instrument is sufficiently robust to perform reliable measurements of static and dynamic tissue optical properties. In addition, the signal-to-noise ratio of the measurements is high enough to observe pulsatile blood flow changes even at longer pathlengths (low probability events), and the instrument can clearly discriminate between superficial and deep-tissue blood flow changes.

The skilled artisan will readily appreciate—and it is worth reiterating—that advantages of the proposed PR-DCS apparatus and method over other instruments that may be targeting pathlength resolved measurements include the fact that the proposed methodology is based on the use of a light source operating in a continuous-wave regime, and that the spatial resolution between different paths through the tissue (along which paths the portion of light from such light source traverses the tissue) is seamlessly controlled with increments defined by the coherence length of such light. Therefore, with the use of an embodiment of the proposed idea there is not photon budget penalty to be paid for measuring long pathlength photons that require large spatial source-detector separations (see $\rho$, FIG. 2), and the detection probabilities of the target species in the tissue are high, whereas most time domain-DCS (TD-DCS) instruments are limited to a source-detector separation of about 1 cm (which shortcoming is well recognized in related art, as evidenced, for example, by Sutin, J. et al. Time-domain diffuse correlation spectroscopy. *Optica* 3, 1006-1013, doi:10.1364/OP-TICA.3.001006, 2016; and Pagliazzi, M. et al. Time domain diffuse correlation spectroscopy with a high coherence pulsed source: in vivo and phantom results. *Biomedical Optics Express* 8, 5311-5325, doi:10.1364/BOE.8.005311, 2017).

With the CW operation of the measurement system, and the resulting measurement is substantially Shott noise-limited, thereby permitting long-separation distances p and long-pathlength measurements to be performed at lower laser powers as compared with those employed in related art. Clearly, therefore, deeper tissues in vivo can be sampled with the PR-DCS than those reachable with currently-existing technology. Furthermore, as a corollary to the use of the CW light source, the measurement system understandably does not require periodic calibrations/corrections based on instrument response, jitter compensations, or phase stabilizations, for example (which are common-use in related art). Finally, practically any off-the-shelf, easy to use, low-cost CW laser diode and standard DCS detector can be used to construct the measurement system according to the idea of the invention. In stark contradistinction to the advantages offered by the disclosed PR-DCS, TD-DCS requires specialized high (long) coherence length pulsed laser sources (and simply cannot be implemented with the CW sources) and high sensitivity, red-enhanced single-photon avalanche diode (SPAD) detectors, while interferometric NIRS requires frequency swept lasers, balanced detectors, and electronics that operate in the GHz range.

For the purposes of this disclosure and the appended claims, the use of the terms "substantially", "approximately", "about" and similar terms in reference to a descriptor of a value, element, property or characteristic at hand is intended to emphasize that the value, element, property, or characteristic referred to, while not necessarily being exactly as stated, would nevertheless be considered, for practical purposes, as stated by a person of skill in the art. These terms, as applied to a specified characteristic or quality descriptor means "mostly", "mainly", "considerably", "by and large", "essentially", "to great or significant extent", "largely but not necessarily wholly the same" such as to reasonably denote language of approximation and describe the specified characteristic or descriptor so that its scope would be understood by a person of ordinary skill in the art. In one specific case, the terms "approximately", "substantially", and "about", when used in reference to a numerical value, represent a range of plus or minus 20% with respect to the specified value, more preferably plus or minus 10%, even more preferably plus or minus 5%, most preferably plus or minus 2% with respect to the specified value. As a non-limiting example, two values being "substantially equal" to one another implies that the difference between the two values may be within the range of +/−20% of the value itself, preferably within the +/−10% range of the value itself, more preferably within the range of +/−5% of the value itself, and even more preferably within the range of +/−2% or less of the value itself. The use of these terms in describing a chosen characteristic or concept neither implies nor provides any basis for indefiniteness and for adding a numerical limitation to the specified characteristic or descriptor. As understood by a skilled artisan, the practical deviation of the exact value or characteristic of such value, element, or property from that stated falls and may vary within a numerical range defined by an experimental measurement error that is typical when using a measurement method accepted in the art for such purposes.

The skilled artisan can now readily appreciate that embodiments of the invention address the operational problems persisting with the use of related art methodology by employing a new PR-DCS approach configured to effectuate depth-sensitive measurements the target tissue (and, in particular—of pulsatile CBF in humans). PR-DCS employs a continuous-wave low coherence interferometer that can be configured to measure CBF changes from tissue depths of at least 3~4 cm below the surface—sufficient to be sensitive to the entire cerebral cortex and even some sub-cortical structures. Critically, in various embodiments, PR-DCS realizes these CBF measurements with readily available laser diodes and conventional DCS detection systems, as it does not require the use of pulsed lasers, frequency-modulated light sources, or custom detector configurations typically used in other pathlength resolved instruments of related art.

While the invention is described through the above-described exemplary embodiments, it will be understood by those of ordinary skill in the art that modifications to, and variations of, the illustrated embodiments may be made without departing from the inventive concepts disclosed herein. Disclosed aspects, or portions of these aspects, may be combined in ways not listed above. Accordingly, the invention should not be viewed as being limited to the disclosed embodiment(s).

What is claimed is:

1. A method for performing a pathlength-resolved diffuse correlation spectroscopy (PR-DCS) measurement of a target tissue, the method comprising:

directing a first portion of a spatially multi-mode light that has an electric field and a coherence length and that is generated by a continuous-wave light source to a first surface area of the target tissue while directing a second portion of the spatially multi-mode light generated by the continuous-wave light source to an optical detection system through a delay line through a single optical channel;

receiving light of the first portion of the spatially multi-mode light, which has traversed the target tissue, at a second surface area of the target tissue as a sample light and directing the sample light through the single optical channel to the optical detection system, wherein the first and second surface areas of the target tissue are spatially separated from one another by a separation distance;

at a single photodetector of the optical detection system;

a) receiving both the second portion of the spatially multi-mode light transmitted through the single optical channel and the first portion of the spatially multi-mode light that has traversed different paths through the target tissue between the first and second surface areas and that has transmitted through the single optical channel, and b) generating a single signal of intensity of interference of the second portion and the first portion of the light at the single photodetector, wherein the intensity of the interference includes both a coherent contribution of the first and second portions of the spatially multi-mode light and an incoherent contribution of the first and second portions received at the single photodetector while switching between first and second of the different paths only by adjusting a delay in the delay line, and with the use of electronic circuitry, configured to receive the single signal of the intesity of the interference from the single photodetector:

identifying a pathlength-resolved autocorrelation function of the electric field based on a pathlength-resolved intensity autocorrelation function of the single signal of the intensity of the interference and a variable that is dependent on a path of the first portion of the spatially multi-mode light through the target tissue;

determining a blood flow in the target tissue at least in part by numerically fitting the pathlength-resolved autocorrelation function of the electric field to a negative exponential that is dependent on the blood flow.

2. A method according to claim 1, wherein the directing the first portion of the spatially multi-mode light to the first surface area includes at least one of:

(a) directing the first portion of the spatially multi-mode light having a coherence length of at least 0.05 mm;

(b) directing the first portion of the spatially multi-mode light generated by the continuous-wave light source that is configured to generate spatially multi-mode distribution of the light; and (c) the coherence length being a pathlength resolution of the PR-DCS measurement.

3. A method according to claim 2, wherein the switching between first and second of the different paths only by the adjusting time delay in the delay line includes switching between the first and second of the different paths with the pathlength resolution defined by the coherence length.

4. A method according to claim 1, wherein at least one of the directing the first portion of the light through the single optical channel and the directing the second portion of the light through the single optical channel includes transmitting light through free space or through an optical fiber.

5. A method according to claim 1, wherein the switching between the first and second of the different paths includes changing a pathlength of the sample light through the target tissue with an increment substantially equal to the coherence length.

6. A method according to claim 1, wherein the continuous-wave light source is configured to generate the spatially multi-mode light having such a degree of coherence that a signal from the signals representing the interference and produced at the optical detection system represents interference between the second portion of the light and the sample light that has traversed a volume of the target tissue at a depth of at least 1 cm below a surface of the target tissue.

7. A method according to claim 1, wherein the continuous-wave light source is configured to generate the spatially multi-mode light having such a degree of coherence that the sample light and the second portion of the light interfere with one another at the optical detection system while at least one of the following conditions is satisfied:

(a) the sample light is produced at the second surface portion that is separated from the first surface portion by the separation distance exceeding 2.5 cm; and (b) the sample light represents the light from the first portion of the spatially multi-mode light that has traversed a pathlength greater than the separation distance.

8. A method according to claim 1, further comprising: determining intensity autocorrelation functions and parameters characterizing the target tissue traversed by each of the different paths through the target by using electronic circuitry configured to receive the signals from the optical detection system.

9. A method according to claim 8, further comprising: numerically determining perfusion in the target tissue based at least on numerically fitting the intensity autocorrelation functions characterizing the target tissue to a negative exponential function, wherein an argument of the negative exponential function includes a product of the perfusion and a squared value of a wave vector representing the sample light but is independent from an absorption coefficient of the target tissue; and determining both a scattering coefficient of the target tissue and the absorption coefficient of the target tissue.

10. A method according to claim 8, further comprising determining values of intensities of the sample light for each of the different paths.

11. A method according to claim 8, wherein the determining includes numerically fitting the intensity autocorrelation functions characterizing the target tissue to a negative exponential function that depends from a wave vector value representing the sample light but is independent from an absorption coefficient of the target tissue.

12. A method according to claim 11, wherein said continuous-wave light source is configured to generate the spatially multi-mode light having such a degree of coherence that the sample light and the second portion of the light interfere with one another at the optical detection system while the sample light represents the light from the first portion of the light that has traversed a pathlength greater than the separation distance.

13. A method according to claim 12, further comprising: recording a parameter of the blood flow at a first rate of lower than 20 Hz or at a second rate between 20 Hz and 100 Hz through the target tissue as a function of a depth of a given path, from the different paths, in the target tissue.

14. A method according to claim 1, further comprising: recording a parameter of the blood flow through the target tissue as a function of a depth of a given path, from the different paths, in the target tissue.

15. A method according to claim 14, wherein the recording the parameter of the blood flow includes recording the parameter of the blood flow at a rate of:

(a) lower than 20 Hz; or (b) between 20 Hz and 100 Hz; or (c) greater than 100 Hz.

16. A method according to claim 1, the method being devoid of using a source of pulsed light or a light source configured to generate modulated light.

17. A method according to claim 1, wherein the directing the first portion of the spatially multi-mode light to the first surface area includes directing the first portion of the spatially multi-mode light generated by the continuous-wave light source.

18. A method according to claim 17, wherein the continuous-wave light source is configured to generate the spatially multi-mode light having such a degree of coherence that the sample light and the second portion of the light interfere with one another at the optical detection system while the sample light represents the light from the first portion of the spatially multi-mode light that has traversed a 5 pathlength greater than the separation distance.

19. A method according to claim 17, further comprising:
recording a parameter of the blood flow at a first rate of lower than 20 Hz or at a second rate between 20 Hz and 100 Hz through the target tissue as a function of a depth 10 of a given path, from the different paths, in the target tissue.

20. A method according to claim 1, further comprising:
recording a parameter of the blood flow at a first rate of lower than 20 Hz or at a second rate between 20 Hz and 15 100 Hz through the target tissue as a function of a depth of a given path, from the different paths, in the target tissue.

* * * * *